United States Patent
Lamoureux et al.

(10) Patent No.: US 7,278,972 B2
(45) Date of Patent: Oct. 9, 2007

(54) COMBINED BONE MARROW ASPIRATION AND CORE BIOPSY DEVICE

(75) Inventors: Gary A. Lamoureux, Woodbury, CT (US); Richard A. Terwilliger, Southbury, CT (US)

(73) Assignee: WorldWide Medical Technologies, LLC, Oxford, CT (US)

( * ) Notice: Subject to any disclaimer, the term of this patent is extended or adjusted under 35 U.S.C. 154(b) by 562 days.

(21) Appl. No.: 10/347,966

(22) Filed: Jan. 21, 2003

(65) Prior Publication Data
US 2003/0139688 A1   Jul. 24, 2003

Related U.S. Application Data

(60) Provisional application No. 60/350,536, filed on Jan. 24, 2002.

(51) Int. Cl.
*A61B 10/00* (2006.01)
(52) U.S. Cl. ............ 600/567; 600/562; 600/563; 600/564; 600/655
(58) Field of Classification Search ........ 600/564, 600/563, 565, 567, 562
See application file for complete search history.

(56) References Cited

U.S. PATENT DOCUMENTS

| | | | | |
|---|---|---|---|---|
| 4,702,260 A * | 10/1987 | Wang | | 600/566 |
| 5,012,818 A * | 5/1991 | Joishy | | 600/567 |
| 5,060,658 A * | 10/1991 | Dejter et al. | | 600/566 |
| 5,257,632 A | 11/1993 | Turkel et al. | | |
| 5,324,300 A * | 6/1994 | Elias et al. | | 606/180 |
| 5,373,855 A * | 12/1994 | Skrabal et al. | | 600/563 |
| 5,429,138 A * | 7/1995 | Jamshidi | | 600/566 |
| 5,527,632 A * | 6/1996 | Gardner | | 429/27 |
| 5,538,009 A * | 7/1996 | Byrne et al. | | 600/567 |
| 5,928,162 A * | 7/1999 | Giurtino et al. | | 600/567 |
| 6,007,496 A * | 12/1999 | Brannon | | 600/565 |
| 6,022,324 A * | 2/2000 | Skinner | | 600/566 |
| 6,273,861 B1 * | 8/2001 | Bates et al. | | 600/567 |
| 6,315,737 B1 * | 11/2001 | Skinner | | 600/566 |

\* cited by examiner

*Primary Examiner*—Max F. Hindenburg
*Assistant Examiner*—Jeffrey Hoekstra
(74) *Attorney, Agent, or Firm*—McCormick, Paulding & Huber LLP

(57) ABSTRACT

A combined bone marrow aspiration and core biopsy device. A large bore cannula includes a coaxial stylet which seals both ends of the cannula, allowing fluid to be aspirated through the space between stylet and cannula. Then, a core sample is taken with the cannula after the stylet is retracted.

6 Claims, 2 Drawing Sheets

COMBINED BONE MARROW ASPIRATION AND CORE BIOPSY DEVICE

CROSS REFERENCE TO RELATED APPLICATIONS

Figure 1:
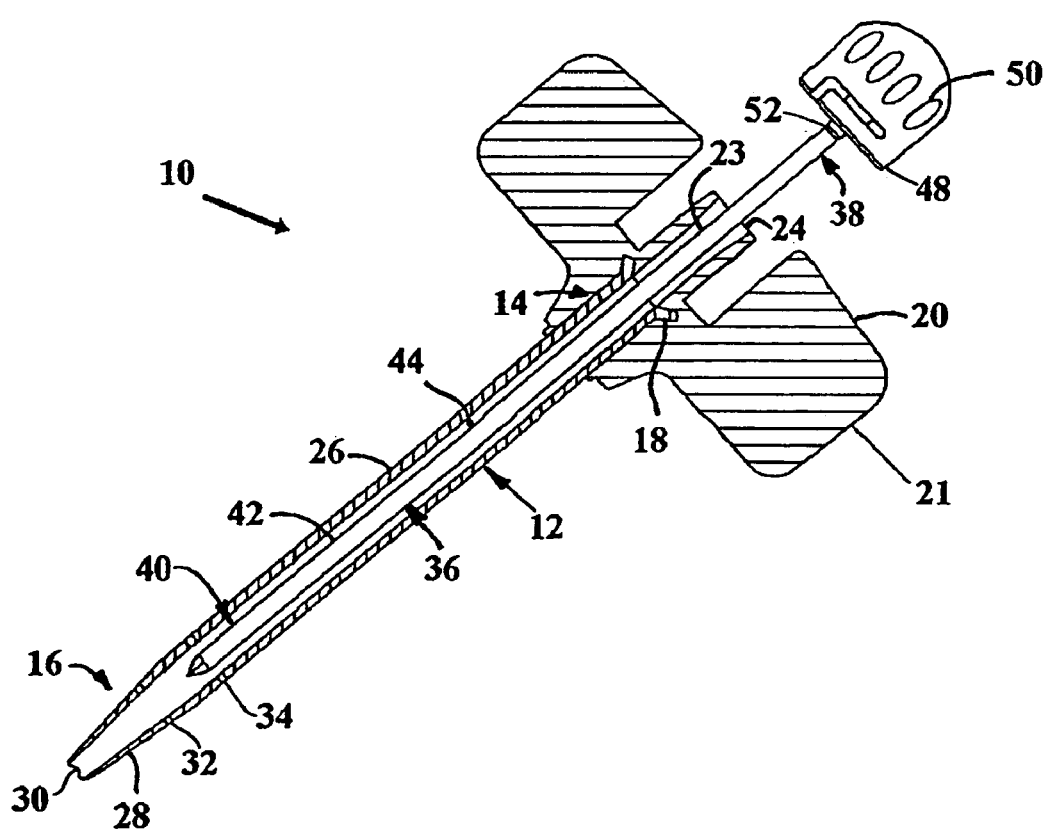

This application claims the benefits of prior filed, co-pending provisional patent application Ser. No. 60/350,536 filed Jan. 24, 2002.

BACKGROUND OF THE INVENTION

A bone marrow biopsy is a test performed by a physician to evaluate bone marrow function. Bone marrow produces red blood cells, white blood cells, and platelets. This test allows the doctor to study these cells in the various stages of development to better plan treatment of bone disease.

The physician may recommend blood tests or special imaging tests such as a bone scan, a CT (or CAT) scan, an MRI, or an angiogram to ascertain the need for intervention into the bone marrow space. A biopsy may be prescribed to remove blood and fluid aspirates from the marrow space as well as a core sample of the bone marrow to determine whether cancer or other disease is present.

In the procedure, two types of samples are required for a full diagnosis. Fluid or aspirate must be drawn from the marrow cavity for cytological study and a core sample of marrow material must be obtained for histological study.

In the conventional prior art procedure, the physician penetrates the hard bone of the patient with a series of different needles from a bone marrow biopsy set. The first needle used is a small bore needle designed to aspirate fluid for cytological study. The small bore needle is twisted down through the cortex of the bone into the marrow space. Once the marrow cavity is accessed, the stylet of the small bore needle is removed and a syringe is attached to the opening where the stylet resides. A fluid sample is withdrawn from the marrow space using the syringe attached to the needle. The bore of the needle used to aspirate fluid must be small so that the small amount of fluid that is available can be drawn up the needle into the syringe. If the needle is too large in internal diameter, there is not enough fluid available to fill the internal volume of the bore and still have enough aspirate fluid available to reach up the full length of the needle and to fill the syringe.

After this aspirated fluid is removed, a second hole must be created in the cortex to obtain a solid marrow sample or core. This second hole is required because the act of aspirating fluid from the marrow dries out the marrow in that area making it unsuitable to obtain a satisfactory marrow core sample.

A large bore needle is used to create this second hole. This larger bore needle is designed with a cylindrical body of a first diameter, tapering to a distal end of a second diameter. The needle is tapered in the last 2 to 3 centimeters of the distal end to a smaller sharpened opening with a cutting edge. This reduced second diameter of the large bore needle assists in capturing and holding the core sample as it is removed from the patient.

Once the hard bone is penetrated, by the large bore needle, the stylet of the needle is removed and the hollow cannula of this second needle is driven into the marrow space to obtain a solid core of marrow. The large bore needle is removed from the patient and the marrow sample is removed. This second needle has a much larger internal bore than the needle used to aspirate, so that the marrow can easily be cored and removed from the marrow cavity.

A bone marrow surgical needle is disclosed in U.S. Pat. No. 5,012,818 to Joishy. Joishy discloses a biopsy needle with a tubular outer sleeve in which two separate conduits are contained. The first conduit is used to obtain the solid bone biopsy sample. The second conduit is used to obtain the fluid bone marrow biopsy sample. Each conduit contains two removable stylets. The handle of the Joishy needle can be opened to remove the stylets from each conduit and attach a syringe to aspirate the bone marrow biopsy sample. The needle is tapered at the cutting end to assist in breaking off and retaining the bone biopsy sample. During use, the needle is pushed into the bone and the handle of the biopsy needle is opened. The first stylet is then removed thereby leaving an opening in the first conduit to receive a solid bone biopsy sample and the handle is again closed. The needle is then pushed further into the bone and the hard bone biopsy sample enters the first conduit. The handle is again opened and the second stylet is removed from the second conduit. A syringe is attached to second conduit at the handle and the bone marrow biopsy sample is aspirated through the second conduit and into the syringe. The needle is then manipulated to assist in breaking off the bone biopsy sample and then removed from the subject.

The Joishy needle requires a sleeve with two conduits and two removable stylets within the conduits. The biopsy procedure requires multiple steps to perform and therefore can be time-consuming. Also, the manufacture of such a complex needle can be difficult and costly.

U.S. Pat. No. 6,007,496 issued Dec. 28, 1999 to Brannon describes a device for harvesting bone, including a hollow cylindrical rod having a sharpened distal end, a proximal end with a handle thereon, and a chamber therein extending axially between the proximal and distal ends. A plunger rod is inserted into the proximal end of the cylindrical rod, the plunger rod being slidable axially within the chamber. A sealing support is provided on the proximal end of the hollow cylindrical rod for engaging the plunger rod to establish a slidable hermetic seal therebetween and prevent retrograde flow of air into the chamber from the proximal end of the cylindrical rod. The sleeve also includes a side opening in the cylindrical rod communicating with the chamber, which is connectable to a source of vacuum for evacuating fluid from the chamber into a fluid reservoir connectable to the side opening for collecting fluid therein. The plunger rod must be constantly advanced to compensate for pressure drop due to collapse of the collected sample at the distal end of the cannula.

U.S. Pat. No. 6,022,324 issued Feb. 8, 2000 to Skinner shows a biopsy instrument, which can be used to take a bone biopsy sample or a soft tissue biopsy sample. The biopsy instrument includes a biopsy needle and a biopsy gun. In operation, a triggering mechanism actuates a firing mechanism causing the cradle together with the needle and the attached syringe to fire forward with a sufficient force such that the needle penetrates the target tissue organ causing a first tissue sample to be cored in the needle. The disposable syringe can then be used to obtain a second tissue sample up through the biopsy needle using a vacuum created in the disposable syringe when the plunger is maintained in a rearward position while the syringe fires forward. In a bone biopsy procedure, the first tissue sample is a bone sample and the second tissue sample is a liquid bone marrow sample. The entire bore of the core sample needle is used to aspirate the fluid sample, which may not be sufficient to fill the needle bore for the full length of the needle.

Skinner employs a retainer projecting into the cannula bore from its larger diameter to retain the cored hard biopsy sample. The sample has a smaller cross-sectional area equal to that of the tapered distal end of the cannula.

It would be desirable to have an improved needle assembly requiring only one entry site into the bone that allows aspirated fluid to be drawn in a sufficient amount for cytological study from the areas adjacent the sides of the needle without disturbing the marrow directly in front of and below the needle tip and that allows the same needle to core the undisturbed marrow in a sufficient amount for histological study from the same needle assembly.

Accordingly, one object of the present invention is to provide an improved needle assembly that requires only one entry site into the bone to obtain aspirate fluid and bone marrow core sample.

Another object of the invention is to provide an improved needle assembly that allows aspirated fluid to be drawn from the areas adjacent to the sides of the needle and allows the same needle to core the undisturbed marrow directly in front of and below the needle tip.

SUMMARY OF THE INVENTION

Briefly stated the invention is an improvement in a combined bone marrow aspiration and core biopsy device of the type having a cannula with proximal and distal ends, the cannula having a wall including a cylindrical wall portion of a first internal diameter extending between its proximal and distal ends, and having a tapered wall portion on its distal end terminating in a distal opening of a second smaller diameter than the first diameter, a cannula handle attached to the cannula proximal end and defining a conduit having a proximal opening, a stylet having a body with proximal and distal ends slidably disposed within the cannula and defining an annular passage between the cannula wall and the stylet body, and a stylet handle attached to the proximal end of the stylet. The improvement comprises a first fluid seal blocking fluid flow from the proximal opening when the stylet is moved to an aspirating position, a second fluid seal simultaneously blocking fluid flow from the distal opening when the stylet is moved to the aspirating position, at least one fluid aspirating port in the cannula wall on the distal end, and at least one fluid collection port in the conduit on the proximal end, whereby fluid may be withdrawn from the aspirating port through the annular space and collected through the collection conduit.

In its preferred embodiment the first fluid seal is a sealing member disposed to be engaged to form a seal between the cannula handle and the stylet handle. The distal end of the stylet body has a diameter between that of the cannula first internal diameter and that of the second smaller diameter, so as to engage the cannula tapered wall portion to close the distal opening when the stylet is moved to the aspirating position. The length of the stylet body and length of the cannula are such that the two fluid seals are made at the same time.

DRAWINGS

Figure 2:
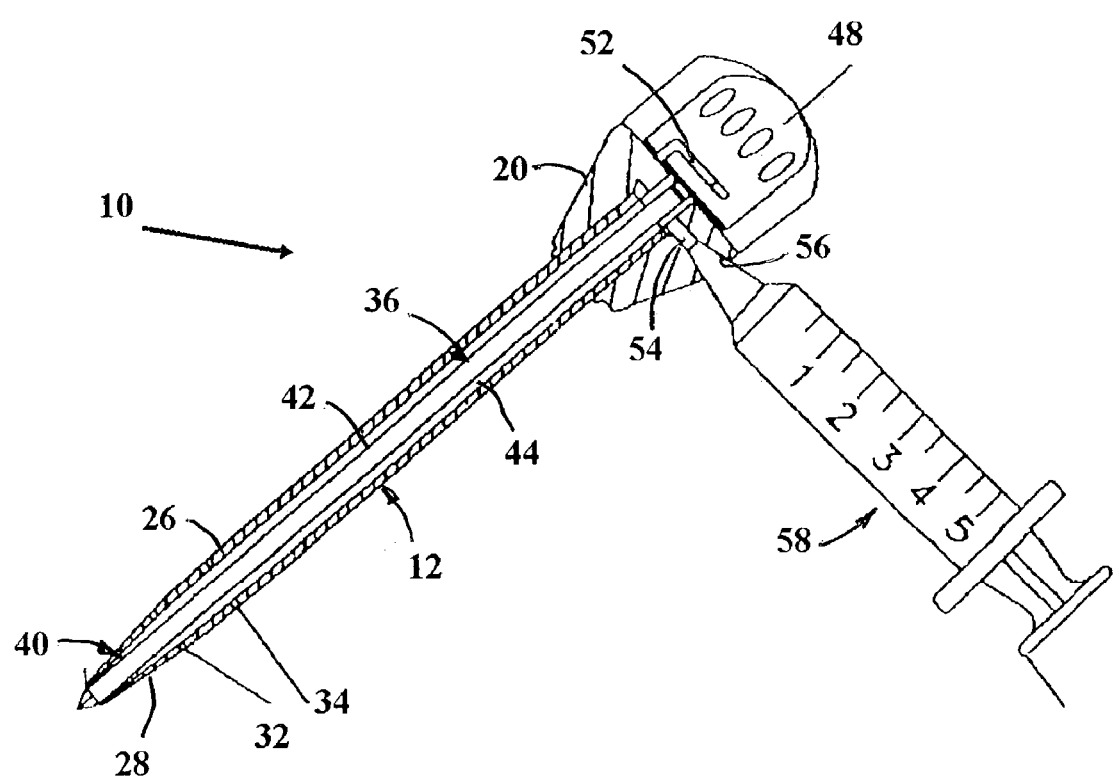

The invention will be better understood by reference to the following description, taken in connection with the accompanying drawings, in which:

FIG. 1 is a front elevational view, partly in cross-section, shown with stylet in a withdrawn position in the cannula, and FIG. 2 is a side elevational view, partly in cross-section, showing the stylet inserted into an aspirating position.

DESCRIPTION OF THE PREFERRED EMBODIMENT

Referring now to FIG. 1 of the drawing, the improved combination bone marrow aspiration and core biopsy device is shown generally at 10 to comprise a cannula 12 with a proximal end 14 and a distal end 16. The proximal end 14 is flared at 18 and embedded in a cannula handle 20, which is preferably of plastic material. The handle includes handle extensions 21 to enable manual manipulation to force the cannula tip through the bone cortex. The open proximal end of the cannula communicates with a conduit 23 that terminates in a proximal opening 24 facing the stylet handle 20.

Cannula 12 is constructed as a large bore hollow metal needle of a type well known in the art for collecting a biopsy core sample. Cannula 12 includes a cylindrical wall portion 26 of a first internal diameter connecting with a tapered wall portion 28. The tapered wall portion 28 terminates in a distal opening 30, which has a second smaller diameter.

The internal diameter of the cannula lies in the range between 0.65 and 0.165 inches, and is preferably on the order of 0.121 inches. The second smaller diameter of the distal opening lies in the range between 0.045 and 0.138 inches, and is preferably on the order of 0.096 inches. The length of the cannula cylindrical portion is about 3.0 inches and the length of the tapered portion is about 1.0 inches. The dimensions are suitable for capturing a core sample of marrow material in a manner welt known in the art.

In order to aspirate fluid from the areas adjacent to the sides of the cannula and to allow the same needle to core the undisturbed marrow directly in front of and below the needle tip, one or more aspirating ports are provided in the cannula wall. These are shown as a port 32 in the tapered portion and a port 34 in the cylindrical portion. Additional aspirating ports (not shown) may be added.

Slidably disposed within the cannula 12 is a stylet (or trocar) 36 having a proximal end 38 and a distal end 40. Extending between the proximal and distal ends is a cylindrical body 42. The space between the wall of cannula cylindrical portion 26 and the stylet body 42 comprises an annular passage 44. The distal end 40 of the stylet has a diameter in between that of the first and second diameters of the cannula. In the embodiment shown, the diameter of the stylet distal end 40 and the diameter of the stylet body 42 are the same, but they need not be so. The diameter of the stylet body may either be larger or smaller than that of the stylet distal end in order to adjust the volume of the annular passage 44.

Attached to the proximal end of stylet 36 is a stylet handle 48. It is provided with gripping surfaces 50 in order to manually manipulate it, while holding the extensions 21 of the cannula handle 20, to slide the stylet in the cannula between a withdrawn position shown in FIG. 1 to an aspirating position shown in FIG. 2.

In accordance with one aspect of the present invention, a sealing member 52 is disposed at the proximal end 38 of the stylet. Sealing member 52 is shown as a tapered member designed and arranged to enter the proximal opening 24 to provide a first fluid seal. Sealing member 52 may either be a separate elastomeric piece threaded over the stylet body or may be an integral part of the stylet handle plastic molding. Although it is shown as a tapered member designed to enter the opening 24, it may also comprise a yieldable member covering and blocking off opening 24 as the stylet is advanced.

In accordance with the present invention, the length of the stylet body is such that when the first fluid seal is made, the stylet distal end also simultaneously engages the tapered wall portion 28 of the cannula to form a second fluid seal.

Reference to FIG. 2 of the drawing shows further details of the improved combination bone marrow aspiration and core biopsy device 10. The device has been rotated about its axis to reveal that collection conduit 54 is provided in the cannula handle 20 which communicated with annular passage 44 through a collection port 56. A syringe 58 may be inserted into the collection conduit 54 to collect aspirated fluid, as shown.

Also in FIG. 2, the stylet 36 is shown advanced to an aspirating position. In this position the first fluid seal is formed by sealing member 52 and the second fluid seal is formed by the distal end of 40 simultaneously engaging the smaller diameter of the tapered wall portion. In this position the fluid may be aspirated from the undisturbed bone marrow area behind the cannula tip through the annular passage 44, collection conduit 56 into the syringe. Because the volume in the annular space 44 is very small, a very small sample may be withdrawn without the problem of filling the entire length of a large bore needle.

Operation

With the inventive device, multiple needles are eliminated as well as multiple points of entry into the bone. The large bore inventive device, with the stylet in place, is twisted through the cortex of the bone. Keeping the stylet in place, the large bore needle is first advanced into the marrow 2 to 3 centimeters to assure the aspirating ports 32, 34 of the cannula are down into the marrow space. The syringe 38 is attached to a port of the collection conduit in the side of the large bore cannula handle that accesses the annular passage between the cannula and the stylet of the assembly. Suction is drawn with the syringe, because the stylet is sealed at the proximal end of the handle with a seal and the stylet distal tip is blocking the tapered distal end of the open cannula.

Fluid is drawn through the aspirating ports of the cannula and aspirated up into the syringe. The stylet body 42 is of sufficient size as to reduce the overall internal volume of the large bore cannula thus allowing what fluid is available in the marrow space to be able to fill this reduced annular passage within the needle and still have sufficient fluid left to fill the syringe.

Once an aspirated sample is withdrawn into the syringe, the syringe is removed and the stylet of the needle is pulled out of the cannula bore. The large bore cannula is driven down into the marrow space to obtain a core sample of marrow material and the needle assembly is then withdrawn from the patient.

The improvements claimed for this inventive combined aspiration and marrow-coring needle are:

1) A needle assembly that requires only one entry site into the bone to obtain aspirate fluid and bone marrow core sample;
2) A needle assembly that allows aspirated fluid to be drawn from the areas adjacent to the sides of the needle and allows the same needle to core the undisturbed marrow directly in front of and below the needle tip;
3) A needle assembly that reduces the overall time a bone marrow biopsy procedure is preformed in with less trauma to the patient;
4) A needle assembly so constructed as to allow the stylet to remain in place during the aspiration of fluid thus minimizing the internal volume within the needle where the fluid flows allowing a large bore needle to be used for the withdrawal of fluid into an attached syringe;
5) A needle assembly that provides a large bore opening of sufficient size as to allow the collection of solid marrow material from the bone;
6) A means to attach a syringe to the needle assembly handle with the stylet of the large bore needle still in place;
7) A needle assembly where the stylet remains in place to close off the open end of the large bore needle during the withdrawal of fluid aspirate;
8) A needle assembly that provides for a side hole or multiple side holes piercing the outer body of the large bore needle near the distal tip to allow fluid to pass into the internal diameter of the large bore needle while the open distal end of the large bore needle is closed off by the stylet being in place;
9) A needle assembly that includes a fluid tight seal on the stylet rod at the proximal end creating a sealed fluid pathway from the distal tip of the cannula into the attached syringe.

While there has been described what is considered to be the preferred embodiment of the invention, other modifications will occur to those skilled in the art, and it is desired to secure in the present application all such modifications as fall within the true spirit and scope of the invention.

The invention claimed is:

1. An improved combined bone marrow aspiration and core biopsy device of the type having a cannula with proximal and distal ends adapted to capture a core sample of bone marrow, the cannula having a wall extending between its proximal and distal ends including a cylindrical wall portion of a first internal diameter and having a tapered wait portion on its distal end terminating in a distal opening of a second smaller diameter than the first diameter, a cannula handle attached to the cannula proximal end and defining a conduit communicating with said cannula and having a proximal opening, a stylet having a body with proximal and distal ends slidably disposed within the cannula and defining an annular passage between the inside of the cannula cylindrical wall portion and the outside of the stylet body, and a stylet handle attached to the proximal end of the stylet, wherein the improvement comprises:

a first fluid seal blocking fluid flow through said proximal opening when the stylet is moved to an aspirating position.

a second fluid seal simultaneously blocking fluid flow through said distal opening when the stylet is moved to said aspirating position, at least one fluid aspirating port in the cannula wall on the distal end thereof communicating with said annular passage adjacent the distal end of the cannula, and at least one fluid collection port communicating with the annular passage adjacent the proximal end of the cannula, whereby fluid is withdrawn from outside the cannula, through the aspirating ports through said annular passage and collected through the collection port.

2. The improvement according to claim 1, wherein the first fluid seal comprises a sealing member disposed to be engaged between the cannula handle and the stylet handle, when the stylet is moved to said aspirating position.

3. The improvement according to claim 1, wherein said second fluid seal is made between the stylet distal end and the cannula tapered wall portion.

4. The improvement according to claim 1, wherein said at least one fluid aspirating port is an opening through the cannula tapered wall portion.

5. The improvement according to claim 1, including a collection conduit defined in the cannula handle and communicating with said fluid collection port.

6. An improved combined bone marrow aspiration and core biopsy device of the type having a cannula with proximal and distal ends adapted to capture a core sample of bone marrow, the cannula having a wall extending between its proximal and distal ends including a cylindrical wall portion of a first internal diameter and having a tapered wall portion on its distal end terminating in a distal opening of a second smaller diameter than the first diameter, a cannula handle attached to the cannula proximal end and defining a conduit communicating with said cannula and having a proximal opening, a stylet having a body with proximal and distal ends slidably disposed within the cannula and defining an annular passage between the inside of the cannula cylindrical wall portion and the outside of the stylet body, and a stylet handle attached to the proximal end of the stylet, wherein the improvement comprises:

a first fluid seal blocking fluid flow through said proximal opening when the stylet is moved to an aspirating position comprising a yieldable sealing member disposed to be engaged between the cannula handle and the stylet handle, a second fluid seal simultaneously blocking fluid flow through said distal opening when the stylet is moved to said aspirating position, wherein the distal end of the stylet body has a diameter between that of the cannula first internal diameter arid that of the second smaller diameter, said second fluid seal being made between the stylet distal end and the cannula tapered wall portion so as to close said distal opening, at least one fluid aspirating port in the cannula wall on the distal end thereof communicating with said annular passage adjacent the distal end of the cannula, and at least one fluid collection port communicating with the annular passage adjacent the proximal end of the cannula, whereby fluid is withdrawn from outside the cannula, through the aspirating port, through said annular passage and collected through the collection port.

* * * * *

UNITED STATES PATENT AND TRADEMARK OFFICE
CERTIFICATE OF CORRECTION

PATENT NO. : 7,278,972 B2 Page 1 of 1
APPLICATION NO. : 10/347966
DATED : October 9, 2007
INVENTOR(S) : Gary Lamoureux and Richard A. Terwilliger It is certified that error appears in the above-identified patent and that said Letters Patent is hereby corrected as shown below:

Column 6, line 31, claim 1 the word "wait" should be replaced with --wall--.

Column 6, line 56, claim 1 the word "ports" should be replaced with --port,--.

Column 8, line 7, claim 6 the word "arid" should be replaced with --and--.

Signed and Sealed this

Thirteenth Day of May, 2008

JON W. DUDAS
*Director of the United States Patent and Trademark Office*